United States Patent [19]

Schwarz et al.

[11] Patent Number: 5,233,045
[45] Date of Patent: Aug. 3, 1993

[54] PROCESS FOR THE PREPARATION OF IMIDAZOTHIAZOLONE DERIVATIVES

[75] Inventors: Michael Schwarz, Gross-Gerau; Michael Casutt, Heppenheim, both of Fed. Rep. of Germany

[73] Assignee: Merck Patent Gesellschaft mit Beschrankter Haftung, Darmstadt, Fed. Rep. of Germany

[21] Appl. No.: 883,510

[22] Filed: May 15, 1992

[30] Foreign Application Priority Data

May 17, 1991 [DE] Fed. Rep. of Germany ....... 4116157

[51] Int. Cl.⁵ .............................................. C07D 513/02
[52] U.S. Cl. ......................................... 548/154; 560/8
[58] Field of Search ............................. 548/154; 560/8

[56] References Cited

U.S. PATENT DOCUMENTS

| | | | |
|---|---|---|---|
| 4,732,987 | 3/1988 | Poetsch et al. | 548/303.7 |
| 4,877,882 | 10/1989 | Poetsch et al. | 548/303.7 |
| 4,937,351 | 6/1990 | Poetsch et al. | 548/303 |

FOREIGN PATENT DOCUMENTS

| | | | |
|---|---|---|---|
| 242686 | 4/1987 | European Pat. Off. | 548/154 |
| WO85/02187 | 5/1985 | PCT Int'l Appl. | 548/154 |

OTHER PUBLICATIONS

English translation of example 1f of WO/85/02187. (1985).

*Primary Examiner*—Mary C. Lee
*Assistant Examiner*—Joseph K. McKane
*Attorney, Agent, or Firm*—Millen, White, Zelano & Branigan

[57] ABSTRACT

The invention relates to a novel process for the preparation of imidazothiazolone derivatives of formula I, wherein $R^1$, $R^2$, $R^3$ and $R^4$ are as defined in the claims, which are suitable for the preparation of D-(+)-biotin.

13 Claims, No Drawings

PROCESS FOR THE PREPARATION OF IMIDAZOTHIAZOLONE DERIVATIVES

The invention relates to a novel process for the preparation of an imidazothiazolone derivative of formula I:

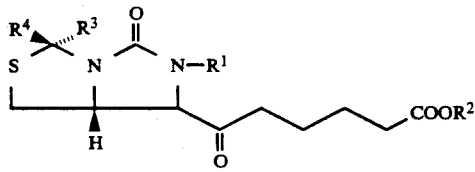

wherein
$R^1$ is H or a protecting group suitable for nitrogen,
$R^2$ is H or alkyl having 1–5 C atoms, and
$R^3$ and $R^4$ in each case independently of one another are H, alkyl having 1–5 C atoms, cycloalkyl having 3–7 C atoms, aryl having 6–10 C atoms, heteroaryl having 5–9 C atoms or aralkyl having 7–10 C atoms, or taken together are alkylene or heteroalkylene having 3–7 C atoms in each case.

Heteroaryl refers to mono- or bicyclic groups with one or two O, N and/or S hetero atoms. Heteroalkylene refers to alkylene groups containing one or two —O—, —NH—, or —S—groups.

Processes for the preparation of these compounds are known, e.g., from German Patent Documents 36 13 245 A1 and 37 03 872 A1. They can be used as intermediates for the preparation of D-(+)-biotin.

For example, in these known processes, a phosphorus ylide of formula II:

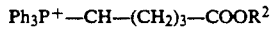

wherein $R^2$ is as defined and Ph is phenyl, is reacted with an imidazothiazolone derivative of formula III:

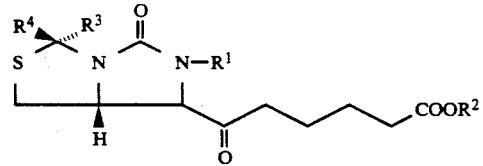

wherein $R^1$, $R^3$ and $R^4$ are as defined.

The ylide II is prepared from a phosphonium halide of formula IV:

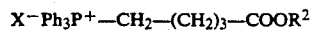

wherein X is Br or Cl and Ph and $R^2$ are as defined. However, the reaction conditions, especially those for producing the ylide, only permit reactions with moderate yields.

SUMMARY OF THE INVENTION

An object of the invention was to develop an improved process for the preparation of the imidazothiazolone derivatives of formula I.

It has now been found, surprisingly, that in the conversion of IV to II, the yield and hence the efficiency of this reaction step can be substantially improved by using lithium hexamethyldisilazide and by changing the reaction conditions.

The invention therefore relates to a process for the preparation of an imidazothiazolone derivative of formula I by reacting a phosphorus ylide of formula II with an imidazothiazolone derivative of formula III, characterized in that the compound of formula II is prepared from a phosphonium halide of formula IV by reaction with lithium hexamethyldisilazide.

In formulae I and II, the radical $R^1$ is H or a protecting group suitable for nitrogen. The expression "protecting group suitable for nitrogen" is generally known and refers to groups which are suitable for protecting (blocking) the nitrogen atom in the molecule of the compound I from chemical reactions, but which are readily removable after the desired chemical reaction has been carried out at another site on the molecule. As the protecting groups are removed after the desired reaction or reaction sequence, their nature and size are moreover not critical. A preferred protecting group $R^1$ is unsubstituted benzyl, but $R^1$ can also be, e.g., benzyl substituted by one or two $C_1$–$C_4$-alkyl and/or $C_1$–$C_4$-alkoxy groups, as well as $C_3$–$C_5$-alk-2-enyl or $C_3$–$C_6$-trialkylsilyl. In the case of multiple substitution, preferable disubstitution, of a phenyl ring, the substituents are preferably identical, although they can also be different. They are preferably located in the 4-position and/or 2-position, but they can also occupy the 3-, 5- and/or 6-positions.

The radical $R^2$ is preferably hydrogen, methyl or ethyl. The radicals $R^3$ and $R^4$ taken together can be alkylene or heteroalkylene having 3–7 C atoms, but are preferably each independently of one another H, alkyl, especially methyl or ethyl, aryl, especially phenyl, or aralkyl, especially benzyl. Particularly preferably, one of these radicals is H and the other is phenyl.

X is preferably Br.

Compounds of formula IV can be prepared by methods known per se, such as those known, e.g., from Houben-Weyl, Methoden der Organischen Chemie (Methods of Organic Chemistry), Vol. 5/16, Vol. 12/1 or Vol. 12/2 (Thieme Verlag, Stuttgart, 4th edition).

II is prepared by means of lithium hexamethyldisilazide. The lithium reagent can be prepared by treating hexamethyldisilazane with one equivalent of an alkyllithium compound, preferably n-butyllithium in n-hexane, or else methyllithium, at temperatures of between −30 and +40, preferably at −10° to 25° and particularly preferably at 10°–15°, over a period of 1–60 minutes, preferably 10–20 minutes, in an inert gas atmosphere; it is normally used in situ.

Thus, the reaction mixture can then be added dropwise, either undiluted or diluted by an inert solvent, preferably tetrahydrofuran (THF), hexane or pentane, to a solution or suspension of IV. Examples of suitable solvents or suspending agents for IV have already been mentioned.

The reaction time is 0.5–3 hours and temperatures of between 0° and 30° are recommended.

The nitriles of formula III can be prepared by methods known per se, such as those described, for example, in German Patent Documents 36 13 245 A1 and 37 03 872 A1 and the literature references cited therein.

Compound II is synthesized by the reaction between lithium hexamethyldisilazide and the phosphoniumbromide IV. The amount of the used compounds ranges between some millimoles and a few moles. Typically, 1 equivalent of compound IV is reacted with 1.5 to 4 equivalents lithium hexamethyldisilazide to yield compound II. Compound II is reacted subsequently with 0.5 to 1.0 equivalents (relative to IV) of compound III to yield compound I. The yield of imidazothiazolone derivative ranges between 65 and 95%, typical of analytical purity.

To react II with III, it is convenient to place one reactant in the reaction vessel and add the second component dropwise at a temperature of between 0° and 50°, preferably at 20°-30°, and then to stir the reaction mixture, preferably for about 5-180 minutes at room temperature, in order to bring the reaction to completion.

For this purpose, the nitrile III is dissolved in an inert solvent, e.g., an ether, preferably diethyl ether, THF or dioxane, a ketone such as acetone, diethyl ketone or methylisobutyl ketone, or a hydrocarbon such as hexane, pentane or cyclohexane, or in a mixture of said solvents.

Particularly preferably, III is dissolved in THF or a mixture of THF and hexane and a dilute solution of II in a mixture of THF and hexane is added dropwise at a temperature of between 20 and 30°.

The compounds of formula I obtained in this way can be converted to one another by esterification or saponification known per se and reacted further to give D-(+)-biotin in accordance with the information in German Patent Documents 36 13 245 A1 and 37 03 872 A1.

The process according to the invention thus affords an improved preparation of the D-(+)-biotin precursor I in high yields using readily available, inexpensive starting materials.

In the Examples which follow, "conventional working-up" means:

Water or dilute mineral acid is added if necessary, the mixture is extracted with an organic solvent such as ethyl acetate, chloroform or methylene chloride, the organic phase is separated off, dried over sodium sulfate, filtered, treated with silica gel/activated charcoal, filtered again and evaporated and the residue is purified by chromatography and/or crystallization.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, ponding German application P 41 16 157.2, filed Nov. 19, 1992 are hereby incorporated by reference.

EXAMPLES

EXAMPLE 1

74.3 g of hexamethyldisilazane are added dropwise at 15° to 275 ml of a solution of n-butyllithium in n-hexane (1.6 molar), placed in a reaction vessel under an $N_2$ atmosphere, and the mixture is stirred for 15 minutes while warming up to room temperature. After dilution with 200 ml of THF, the reaction mixture, which contains lithium hexamethylsilazide, is added dropwise to a suspension of 88.7 g of 4-carboxybutyltriphenylphosphonium bromide in 300 ml of THF and the resulting mixture is stirred for a further 15 minutes at room temperature. The solution now contains the corresponding ylide.

50.3 g of a mixture of (7R,7aR)- and (7S,7aR)-3-phenyl-6-benzyl-7-cyano-7,7a-dihydro- b 1H,4H-imidazo[1,5-c]thiazol-5(6H)-one, dissolved in 150 ml of THF, are then added dropwise to this solution, again at room temperature. The resulting mixture is stirred for a further 1.5 hours to give 46.0 g of 3-phenyl-6-benzyl-7-(5-carboxy-1-oxopentyl)-7,7a-dihydro-1H,3H-imidazo[1,5-c]thiazol5(6H)-one after conventional working up.

EXAMPLE 2

Analogously to Example 1, 47.3 g of 3-phenyl-6benzyl-7-(5-methoxycarbonyl-1-oxopentyl)-7,7a-dihydro-1H, 3H-imidazo[1,5-c]thiazol-5(6H)-9-one are obtained starting from 92.4 g of 4-methoxycarbonylbutyltriphenyl-phosphonium bromide by reaction with lithium hexamethylsilazide and subsequent reaction of the product with 51.2 g of a mixture of (7R,7aR)- and (7S,7aR)-3-phenyl-6benzyl-7-cyano-7,7a-dihydro-1H,3H-imidazo[1,5-c]thiazol-5(6H)-one.

$[\alpha]^{25}_D = -171.3°$, c=1 (benzene).

EXAMPLE 3

Analogously to Example 1, 48.7 g of 3-phenyl-6-benzyl-7-(5-ethoxycarbonyl-1-oxopentyl)-7,7a-dihydr o1H, 3H-imidazo[1,5-c]thiazol-5(6H)-9-one are obtained starting from 99.7 g of 4-ethoxycarbonylbutyltriphenylsilazide and subsequent reaction of the product with 53.7 g of a mixture of (7R, 7aR)- and (7S, 7aR)-3-phenyl-6benzyl-7-cyano-7,7a-dihydro-1H, 3 H-imidazo[1,5-c]thiazol5(6H)-one.

$[\alpha]^{25}_D = 170.0°$, c=1 (benzene).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of an imidazothiazolone derivative of formula I:

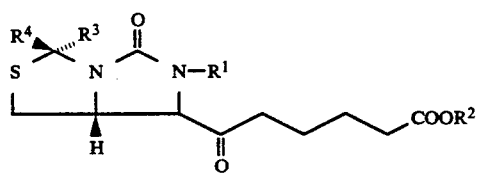

wherein
 $R^1$ is H or a nitrogen protecting group,
 $R^2$ is H or alkyl having 1-5 C atoms, and
 $R^3$ and $R^4$ in each case independently of one another are H, alkyl having 1-5 C atoms, cycloalkyl having 3-7 C atoms, aryl having 6-10 C atoms, heteroaryl having 5-9 C atoms or aralkyl having 7-10 C atoms, or taken together are alkylene or heteroalkylene having 3-7 C atoms in each case, said process comprising reacting a phosphorus ylide of formula II:

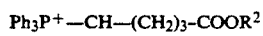

wherein $R^2$ is as defined and Ph is phenyl, with an imidazothiazolone derivative of formula III:

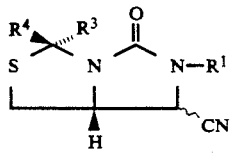

wherein $R^1$, $R^3$ and $R^4$ are as defined, said compound of formula II is prepared by reacting a phosphonium halide of formula IV:

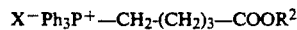

with lithium hexamethyldisilazide.

2. A process according to claim 1, wherein the reaction is conducted at a temperature of between 0° and 50° C.

3. A process according to claim 2, wherein the temperature is 20°-30°C.

4. A process according to claim 1, wherein the reaction mixture is stirred for about 5-180 minutes at room temperature.

5. A process according to claim 1, wherein the imidazothiazolone derivative of formula III is dissolved in an inert solvent selected from an ether, ketone, hydrocarbon or mixtures thereof.

6. A process according to claim 1 wherein $R^1$ is selected from unsubstituted benzyl or benzyl substituted by one or two $C_{1-4}$-alkyl and/or $C_{1-4}$-alkoxy, $C_{3-5}$-alk-2-enyl or $C_{3-6}$-trialkylsilyl.

7. A process according to claim 1, wherein $R^2$ is hydrogen, methyl or ethyl.

8. A process according to claim 1 wherein $R^3$ and $R^4$ are each independently hydrogen and phenyl.

9. A process according to claim 1, wherein X is Br.

10. A process according to claim 6, wherein the imidazothiazolone is dissolved in tetrahydrofuran or a mixture of tetrahydrofuran and hexane.

11. A process according to claim 1, wherein phosphorous ylide of formula II is in a mixture of tetrahydrofuran and hexane.

12. A process according to claim 1, wherein an equivalent phosphonium halide of formula IV is reacted with 1.5 to 4 equivalent of lithium hexamethyldisilazide.

13. A process according to claim 1, wherein 0.5 to 1.0 equivalents of imidazothiazolone derivative of formula III is reacted with phosphorus ylide of formula II.

* * * * *